United States Patent [19]

Jongsma

[11] 4,285,777

[45] Aug. 25, 1981

[54] PROCESS FOR THE PURIFICATION OF BENZALDEHYDE

[75] Inventor: Cornelis Jongsma, Oirsbeek, Netherlands

[73] Assignee: Stamicarbon, B.V., Geleen, Netherlands

[21] Appl. No.: 125,662

[22] Filed: Feb. 28, 1980

[30] Foreign Application Priority Data

Mar. 2, 1979 [NL] Netherlands ......................... 7901670

[51] Int. Cl.$^3$ ............................................. B01D 3/34
[52] U.S. Cl. .................................... 203/32; 568/425; 568/438
[58] Field of Search .................. 568/438, 425; 203/28, 203/29, 32

[56] References Cited

U.S. PATENT DOCUMENTS 2,856,332  10/1958  Mertzweiller ......................... 203/32
3,379,768   4/1968  Corson et al. ....................... 568/438

*Primary Examiner*—Frank Sever
*Attorney, Agent, or Firm*—Cushman, Darby & Cushman

[57] ABSTRACT

A process for purification of impure benzaldehyde by which purified benzaldehyde is prepared which has improved color stability and improved olfactory characteristics. The process is comprised of the steps of treatment with hydrogen in the presence of a hydrogenation catalyst followed by distillation.

The present invention is a new and novel process for the purification of benzaldehyde and, is in particular, a unique and novel process for the purification of benzaldehyde prepared by the oxidation of toluene with a gas containing molecular oxygen.

13 Claims, No Drawings

PROCESS FOR THE PURIFICATION OF BENZALDEHYDE

BACKGROUND OF THE INVENTION

Benzaldehyde is an important starting material in various chemical syntheses, including those relating to the synthesis of scents and flavors. In these applications the benzaldehyde is often required to have a high degree of purity, but unfortunately crude benzaldehyde, and especially benzaldehyde prepared by the oxidation of toluene with a gas containing molecular oxygen will contain certain impurities that are very difficult to remove. One very significant problem presented by these impurities is that it is particularly difficult to obtain a product from such crude benzaldehyde that will satisfy olfactory specifications. Furthermore, the presence of such impurities also causes a quite rapid discoloration of the benzaldehyde during storage. Such discoloration will occur even at very low concentrations of the impurities, such as a few p.p.m. by weight. It is of interest to note that benzyl hydroperoxide is not normally present in the crude benzaldehyde in any significant quantities.

One suggested solution which appears in Japanese Pat. Publication No. 24,467/74 is to purify the crude benzaldehyde by treating it with an aqueous solution of sodium hydroxide. However, this method of purification does not give satisfactory results, as shown, by the fact that benzaldehyde treated in this manner is still found to discolor quite rapidly.

One method which does give satisfactory results is that disclosed in U.S. Pat. application Ser. No. 952,609 filed Oct. 18, 1978. The process disclosed in that application employs an oxidizing agent and a distillation step to accomplish the purification.

Still another method is disclosed in a sister application to the present application filed on the same date in the United States Patent Office. In that application, the difficulty was in trying to purify an impure benzaldehyde in the presence of water. That problem was overcome by treating the impure benzaldehyde simultaneously with water and a metal less noble than hydrogen followed by a distillation step.

DESCRIPTION OF THE INVENTION

The present invention provides an additional process for purifying the crude benzaldehyde. According to the process of the present invention, pure benzaldehyde is obtained by treating impure benzaldehyde, which contains no significant quantities of benzyl hydroperoxide, with hydrogen in the presence of a suitable hydrogenation catalyst to achieve hydrogenation of the impurities without significant hydrogenation of benzaldehyde. This is followed by a distillation step.

One advantage of the process of the present invention is that the loss of benzaldehyde is relatively small, usually in the range of about 1 to 5% by weight, while still producing benzaldehyde with satisfactory olfactory characteristics even if the crude benzaldehyde was prepared by the oxidation of toluene.

Hydrogenation catalysts which are suitable for use in the process of the present invention are the known hydrogenation catalysts such as the metals of Group VIII of the periodic table of elements, e.g., palladium, nickel, platinum, iridium or rhodium. The catalyst may be placed on a typical carrier such as carbon, aluminum oxide, silicon or titanium oxide. Catalyst which are particularly suitable for use in the process of the present invention are Raney nickel and palladium on carbon.

Preferably, the catalyst employed will be used in quantities varying from about 0.5 to about 200 mgat of active substance per kg of benzaldehyde. In particular, quantities of catalyst in the range of from about 1.0 mgat to about 100 mgat of active substance per kg of benzaldehyde may be advantageously used in the present process.

Normally, the amount of hydrogen taken up in purification of the impure benzaldehyde will range from about 1 to about 100 liters of hydrogen (N.T.P.) per kg of benzaldehyde per hour. Often, the amount of hydrogen taken up will be in the range of about 3 to about 40 liters of hydrogen (N.T.P.) per kg of benzaldehyde per hour.

The contacting of hydrogen with the impure benzaldehyde can be done in a number of ways including, for example, by stirring the benzaldehyde in a hydrogen atmosphere or by bubbling hydrogen through or over the impure benzaldehyde. The duration of the hydrogenation process is usually between about 0.25 and about 4 hours and is preferably in the range of from about 0.5 to 2 hours. The use of larger quantities of catalyst and/or of larger excesses of hydrogen eventually during longer treatment periods is acceptable but offer no significant advantages.

Treatment of the impure benzaldehyde with hydrogen in the presence of a suitable hydrogenation catalyst is preferably, effected at a moderate temperature in order to suppress hydrogenation of the benzaldehyde. A suitable temperature range is between about 270 and about 400 K. Particularly suitable are temperatures between about 285 and about 340 K. The reaction pressure should be such that the liquid phase is maintained. A suitable reaction pressure is, for example, between about 100 and about 1000 Kpa. A particularly suitable reaction pressure is in the range of about 100 and about 500 kPa. The distillation subsequent to the hydrogenation treatment may be carried out at atmospheric or elevated pressure, but is preferably conducted at a reduced pressure, for instance, a pressure in the range of between about 2kPa and about 35 kPa.

U.S. Pat. No. 3,387,036 discloses that an oxidation product of toluene, consisting of a mixture of toluene, benzyl hydroperoxide, benzaldehyde, benzoic acid and some other by-products, may be processed in such a manner that the benzyl hydroperoxide is converted, for instance, by catalytic hydrogenation of the benzylhydroperoxide. However, such a "deperoxidation" is completely different from the method of the present invention.

The invention will be elucidated by means of the following non-restrictive examples and comparative experiment. The color value in degrees Hazen (°H) was determined by ASTM D 1209/62.

EXAMPLE I

A sample of benzaldehyde, prepared by oxidation of toluene in the liquid phase by means of a gas containing molecular oxygen with the use of a homogeneous cobalt catalyst, was treated with hydrogen for 2 hours at 295 K. and a pressure of 350 KPa in the presence of 0.5% by wt. Raney nickel, dring which treatment 10 liters hydrogen (N.T.P.) per kg benzaldehyde per hour was taken up. Subsequently, the mixture was distilled in a sieve-tray column with 30 trays at a top pressure of 20 kPa and with a reflux ratio of 1:3. The color value of the main fraction was 10° H. This main fraction was divided into two portions. One portion was heated for 1 hour under a nitrogen atmosphere. The color value rose to 25° H. The other portion was stored for 30 days in a dark bottle under a nitrogen atmosphere. At the end of this period, the color value had risen to 20° H.

EXAMPLE II

A sample of the same liquid crude benzaldehyde as used in Example I was treated with hydrogen for 0.5 hour at 305 K. and a pressure of 300 kPa in the presence of 0.5% by wt. 5% palladium-on-carbon catalyst, during which treatment 30 liters hydrogen (N.T.P.) per kg benzaldehyde per hour was taken up. Subsequently, the mixture was distilled under the same conditions as in Example I. The color value of the main fraction was 10° H. This main fraction was divided into two portions. One portion was heated for 1 hour under a nitrogen atmosphere. The color value rose to 35° H. The other portion was stored for 30 days in a dark bottle under a nitrogen atmosphere. At the end of this period, the color value had risen to 25° H.

Comparative Experiment

A sample of the same liquid benzaldehyde as used in Example I was distilled without previcus treatment, under the same circumstances as in Example I. The color value of the main fraction was 25° H. This main fraction was divided into two portions. One portion was heated under a nitrogen atmosphere. After 0.2 hour, the color value of this portion had already arisen to well over 100° H. The other portion was stored for 30 days in a dark bottle under a nitrogen atmosphere. At the end of this period, the color value had risen to 50° H.

What is claimed is:

1. Process for the purification of impure benzaldehyde including odiferous impurities comprising the steps of:
    (a) treating impure benzaldehyde including odiferous impurities with hydrogen in the presence of a hydrogenation catalyst at conditions of temperature and pressure sufficient to selectively hydrogenate said impurities without hydrogenating said benzaldehyde; and
    (b) distilling said treated benzaldehyde.

2. The process of claim 1, wherein the hydrogenation catalyst contains a metal of group VIII of the periodic table of elements.

3. The process of claim 2, wherein the hydrogenation catalyst is Raney nickel.

4. The process of claim 2, wherein the hydrogenation catalyst is palladium on carbon.

5. The process of claim 1, wherein the amount of hydrogenation catalyst is in the range of from about 0.5 mgat to 200 mgat of active substance per kg of benzaldehyde.

6. The process of claim 5, wherein the amount of hydrogenation catalyst is in the range of from about 1 mgat to about 100 mgat of active substance per kg of benzaldehyde.

7. The process of claim 1, wherein the duration of the treatment with hydrogen is between about 0.25 hours and about 4 hours.

8. The process of claim 7, wherein the duration of the treatment with hydrogen is between about 0.5 and about 2 hours.

9. The process of claim 1, wherein the treatment with hydrogen is effected at a temperature between about 270 K and about 400 K.

10. The process of claim 9, wherein the treatment with hydrogen is effected at a temperature between about 285 K and about 340 K.

11. The process of claim 1, wherein the treatment with hydrogen is effected at a pressure between about 100 and about 1000 kPa.

12. The process of claim 11, wherein the treatment with hydrogen is effected at a pressure between about 100 kPa and about 500 kPa.

13. The process of claim 1, wherein the impure benzaldehyde was obtained by the oxidation to toluene with a gas containing molecular oxygen.

* * * * *